United States Patent
Cullen et al.

(10) Patent No.: US 11,679,023 B2
(45) Date of Patent: Jun. 20, 2023

(54) MANDIBULAR ADVANCEMENT SPLINT

(71) Applicants: Stewart Cullen, Subiaco (AU); Christopher Charles Pantin, Applecross (AU); Valerie Patricia Pantin, Applecross (AU)

(72) Inventors: Stewart Cullen, Subiaco (AU); Christopher Charles Pantin, Applecross (AU); Valerie Patricia Pantin, Applecross (AU)

(*) Notice: Subject to any disclaimer, the term of this patent is extended or adjusted under 35 U.S.C. 154(b) by 109 days.

(21) Appl. No.: 16/739,836

(22) Filed: Jan. 10, 2020

(65) Prior Publication Data

US 2020/0146874 A1 May 14, 2020

Related U.S. Application Data

(63) Continuation of application No. PCT/AU2018/050712, filed on Jul. 11, 2018.

(30) Foreign Application Priority Data

Jul. 11, 2017 (AU) .................. 2017902725

(51) Int. Cl.
*A61F 5/56* (2006.01)
(52) U.S. Cl.
CPC ..................... *A61F 5/566* (2013.01)
(58) Field of Classification Search
CPC .. Y10S 602/902; A61F 2/00; A61F 2005/563; A61F 5/055; A61F 5/05891;
(Continued)

(56) References Cited

U.S. PATENT DOCUMENTS 3,247,844 A * 4/1966 Berghash ............. A63B 71/085
D24/176
3,330,038 A * 7/1967 Berman .................. A61C 7/00
433/72

(Continued)

FOREIGN PATENT DOCUMENTS

KR 101008463 B1 * 11/2011 ............... A61F 5/56
KR 101080463 B1 * 11/2011 ............... A61F 5/56
(Continued)

OTHER PUBLICATIONS

Machine Translation of KR201000064166A [published as KR-101080463-B1] created Feb. 14, 2023 from Espacenet.com (Year: 2011).*

(Continued)

*Primary Examiner* — Ophelia A Hawthorne
*Assistant Examiner* — Gina Mccarthy
(74) *Attorney, Agent, or Firm* — Westman, Champlin & Koehler, P.A.; Amanda M. Prose

(57) ABSTRACT

A mandibular advancement splint)MAS) including dentition engagement units, each having a face for operatively abutting a complementary face of the other, and an opposed dentition engagement face which is adapted to positively engage the maxillary or mandibular dentition. A plane of abutment of the faces is approximately normal to the sagittal plane to facilitate sliding displacement of one engagement unit relative to the other. The MAS further includes at least one elastic element configured to operatively exert a user-configurable urging force between said dentition engagement units, so that the mandibular dentition is biased forward and along said abutment plane relative to the maxillary dentition when the splint is in use.

21 Claims, 4 Drawing Sheets

(58) Field of Classification Search
CPC .... A61C 7/36; A61C 7/00; A61C 7/08; A61C 7/146; A61C 17/08; A61B 5/4818; A61B 5/01; H04R 1/1033; A61M 16/0493; A61M 16/0497; A61M 16/06; A63B 71/085; F16F 3/12
See application file for complete search history.

(56) References Cited

U.S. PATENT DOCUMENTS

| | | | |
|---|---|---|---|
| 5,092,346 | A | 3/1992 | Hays |
| 5,117,816 | A | 6/1992 | Shapiro et al. |
| 5,365,945 | A | 11/1994 | Halstrom |
| 5,409,017 | A | 4/1995 | Lowe |
| 5,427,117 | A | 6/1995 | Thornton |
| 5,499,633 | A | 3/1996 | Fenton |
| 5,562,106 | A | 10/1996 | Heeke et al. |
| 5,566,683 | A * | 10/1996 | Thornton .......... A61M 16/0493 128/859 |
| 5,720,302 | A | 2/1998 | Belfer |
| 5,755,219 | A * | 5/1998 | Thornton .......... A61M 16/0493 128/201.18 |
| 5,810,013 | A | 9/1998 | Belfer |
| 5,823,194 | A | 10/1998 | Lampert |
| 5,868,138 | A | 2/1999 | Halstrom |
| 5,921,241 | A | 7/1999 | Belfer |
| 5,947,724 | A | 9/1999 | Frantz et al. |
| 6,041,784 | A | 3/2000 | Halstrom |
| 6,053,816 | A * | 4/2000 | Immel .................. F16F 3/12 472/105 |
| 6,092,523 | A | 7/2000 | Belfer |
| 6,109,265 | A * | 8/2000 | Frantz .................. A61F 5/566 128/862 |
| 6,161,542 | A | 12/2000 | Halstrom |
| 6,418,933 | B1 | 7/2002 | Strong |
| 6,526,982 | B1 | 3/2003 | Strong |
| 6,604,527 | B1 | 8/2003 | Palmisano |
| 6,729,335 | B1 | 5/2004 | Halstrom |
| 6,767,207 | B1 | 7/2004 | Lampert |
| 6,845,774 | B2 | 1/2005 | Gaskell |
| 7,810,502 | B1 | 10/2010 | Nguyen et al. |
| 2004/0177853 | A1* | 9/2004 | Kownacki ............ A61F 5/566 128/848 |
| 2005/0081859 | A1 | 4/2005 | Scarberry et al. |
| 2006/0196512 | A1* | 9/2006 | Gaskell .................. A61C 17/08 128/859 |
| 2007/0283967 | A1* | 12/2007 | Bailey ................... A61F 5/566 128/848 |
| 2009/0004619 | A1* | 1/2009 | Oda ...................... A61C 7/146 433/10 |
| 2010/0154802 | A1* | 6/2010 | Fuselier ................. A61F 5/566 128/848 |
| 2010/0218773 | A1* | 9/2010 | Thornton .......... A61M 16/0497 128/848 |
| 2011/0003262 | A1 | 1/2011 | Frantz et al. |
| 2011/0259345 | A1* | 10/2011 | Cullen ................... A61F 5/566 433/214 |
| 2012/0073582 | A1 | 3/2012 | Kopp |
| 2012/0251970 | A1 | 10/2012 | Awde |
| 2015/0007830 | A1* | 1/2015 | Remmers ............ A61B 5/4818 29/592 |
| 2015/0216716 | A1 | 8/2015 | Anitua Aldecoa |
| 2015/0225150 | A1* | 8/2015 | Farrell ................. H04R 1/1033 24/16 PB |
| 2017/0056235 | A1* | 3/2017 | Thornton .............. A61B 5/01 |
| 2017/0151086 | A1* | 6/2017 | Fareid .................. A61F 5/566 |
| 2018/0055682 | A1* | 3/2018 | Gillette ................ A61M 16/06 |
| 2018/0078401 | A1* | 3/2018 | Hsu ...................... A61F 5/055 |
| 2018/0168845 | A1* | 6/2018 | Hofmann ............ A61F 5/05891 |
| 2018/0200102 | A1* | 7/2018 | Magness ................ A61F 5/566 |
| 2020/0129270 | A1* | 4/2020 | Hofmann ................ A61C 7/08 |

FOREIGN PATENT DOCUMENTS

| | | |
|---|---|---|
| WO | 2011159360 A1 | 12/2011 |
| WO | 2014197430 A1 | 12/2014 |

OTHER PUBLICATIONS

Machine Translation of KR-101080463 created Nov. 3, 3031 from Espacenet.net (Year: 2011).*

International Search Report dated Aug. 24, 2018 for corresponding International Application No. PCT/AU2018/050712 filed Jul. 11, 2018.

Written Opinion of the International Searching Authority dated Aug. 24, 2018 for corresponding International Application No. PCT/AU2018/050712 filed Jul. 11, 2018.

* cited by examiner

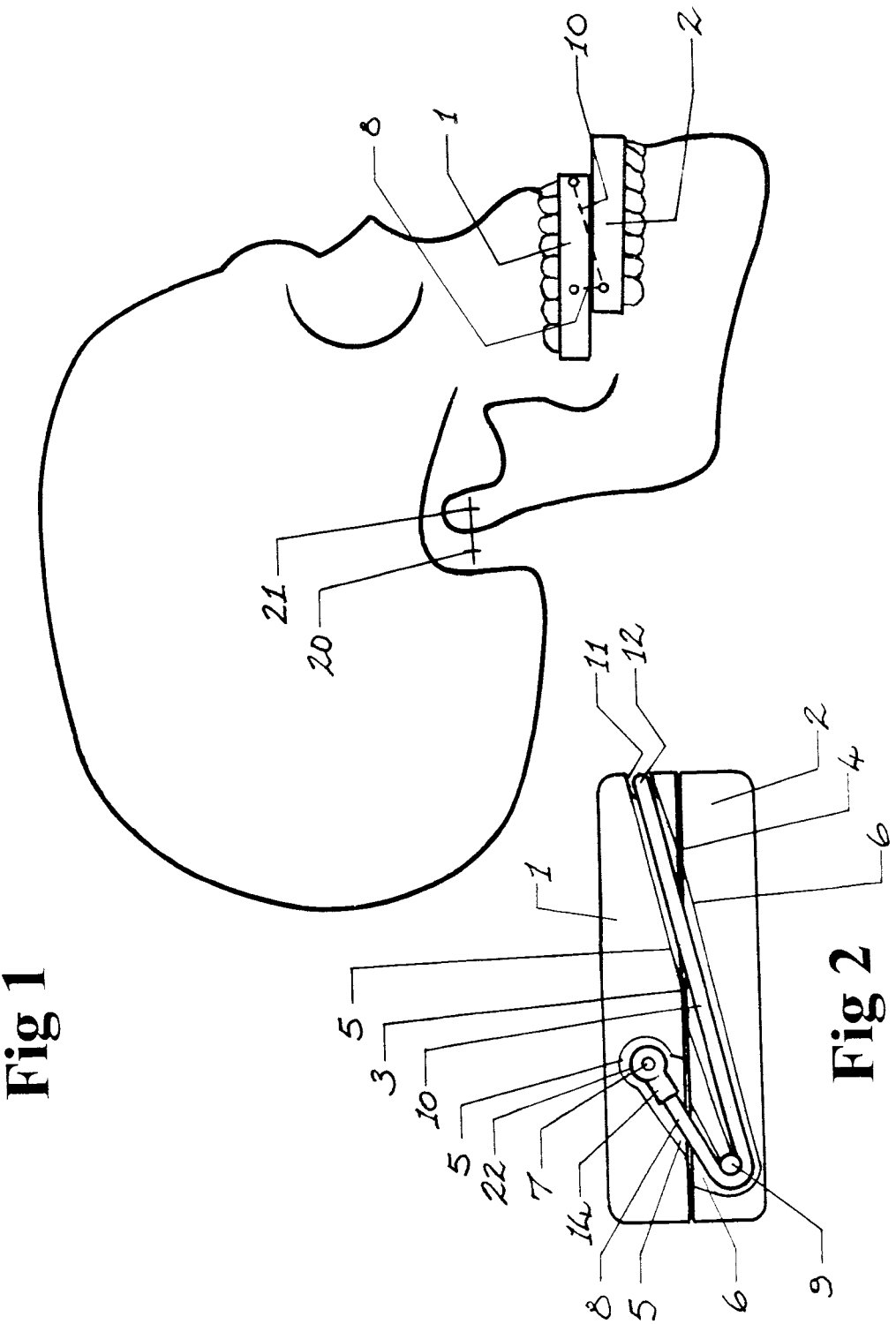

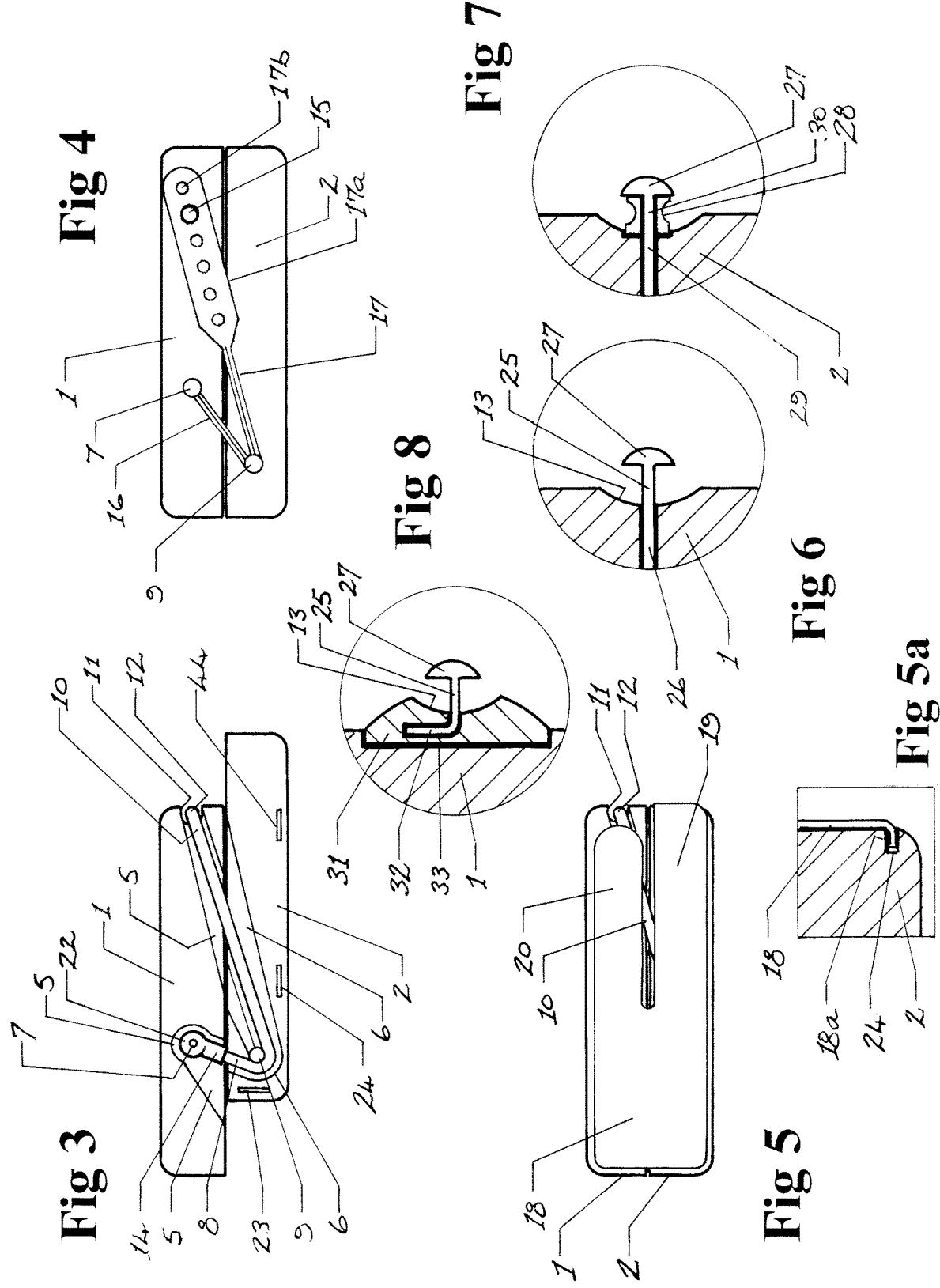

MANDIBULAR ADVANCEMENT SPLINT

CROSS REFERENCE TO RELATED APPLICATIONS

This is a Continuation Application of International Application No. PCT/AU2018/050712, filed Jul. 11, 2018, and published as WO 2019/010528 A1, on Jan. 1, 2019, not in English, which claims priority to and benefits of Australian Patent Application Serial No. 2017902725, filed on Jul. 11, 2017, the entire contents of which are incorporated herein by reference.

TECHNICAL FIELD

This invention relates generally to devices for the alleviation of snoring and sleep apnoea. It relates specifically to such devices which function by utilising elastic tension to induce mandibular advancement during sleep periods.

BACKGROUND ART

The following discussion of the background art is intended to facilitate an understanding of the present invention only. The discussion is not an acknowledgement or admission that any of the material referred to is or was part of the common general knowledge as at the priority date of the application.

During sleep, it is common for airway obstruction to occur as a result of the apposition of the rear part of the tongue or soft palate with the posterior pharyngeal wall. A first result is snoring—the vibration of the oral tissues during respiration—which may be only a nuisance to a partner or perhaps result in sleep interruption. Exacerbated by obesity or loss of muscle tone in throat and oral tissues with aging, the condition may progress to obstructive sleep apnoea. This is a potentially lethal disorder in which breathing stops during sleep for 10 seconds or more for possibly as many as 300 times during a night of sleep. The condition has been associated with a variety of potentially serious medical conditions, such as hypertension, ischaemic heart disease and stroke. It is thus desirable that a diagnosis be made and treatment commenced as early as possible.

Because of the ubiquity of the condition, a very wide variety of treatments has been proposed. These include surgery, positive ventilation methods and the use of many devices designed to provide mandibular advancement, anterior displacement of the tongue or a combination of both. Other treatments, involve the insertion of bone anchors or the implantation of magnets in the uvula. The use of magnets to apply a corrective force to teeth and jaws in orthodontic and orthopaedic procedures is also well known.

It has long been known that anterior displacement of the tongue greatly reduces the tendency for its inner part to relax against the posterior pharyngeal wall, thereby alleviating snoring and, in many cases, sleep apnoea. It is also well known that advancement of the mandible carries the tongue forward in a desirable way. A mandibular advancement of up to 10 millimetres, and normally in the range of five to 10 millimetres, is required to alleviate the symptoms of snoring and sleep apnoea. While there are many devices directed specifically towards forward displacement and control of the tongue, it is the class of devices directed towards mandibular advancement that is of interest to this application.

Almost all devices directed towards mandibular advancement are based upon a pair of separate, approximately arcuately-shaped units which engage the upper and lower dentition. Each of these has one more or less flat face which abuts a complementary face of the other. Each has an opposed dentition engagement face which is adapted to positively engage, as appropriate, all or part of the maxillary or mandibular dentition. The dentition engagement units, commonly referred to as dental overlays or splints, are moulded from dental impressions made in the normal way or created directly by a user. This latter method is performed by the user biting into a quantity of settable resin material provided within the dentition engagement units or enclosing the dentition within thermoplastic pre-forms that have been softened by heating, the material retaining an impression of the dentition following setting or cooling. Where dental impressions are made by biting, the two dentition engagement units are first located in correct juxtaposition. In the simplest method of use, the dentition engagement units are joined or hinged in a way providing the requisite degree of mandibular advancement and closing of the jaws to enter the teeth fully into the dental impressions acts to effect the advancement.

Examples of this type of application are those taught by Heeke et al in U.S. Pat. No. 5,562,106 and Lampert in U.S. Pat. No. 6,767,207. In WO 2011/159360, Grosky teaches the use of an oral appliance for the treatment of snoring and sleep apnea in which the relative positions of the upper and lower dentition engagement units one to another are adjustable by means of a continuous loop of thread passing through pulleys and locked by a locking device. In another application, typified by those taught by Belfer in U.S. Pat. Nos. 5,720,302, 5,810,013 and 5,921,241, tension is simply maintained on a lower dentition engagement unit through an extension member connected to an oral shield bearing against the external surfaces around the mouth or upper lip.

In other applications, the two dentition engagement units are joined by struts, cams, wedges, springs, elastic bands, hooks, screws or combinations thereof to exert an advancement force upon the lower dentition engagement unit and, thereby, to advance the mandible. Examples of such devices in which some form of ramp or wedging element fixed to an upper dentition engagement unit is employed to effect mandibular advance by exerting a force against the lower dentition or a lower dentition engagement unit are known in the prior art.

Examples are those taught by Belfer in U.S. Pat. No. 6,092,523, Palmisano in U.S. Pat. No. 6,604,527, Thornton in U.S. Pat. Nos. 5,427,117 and 5,566,683, Shapiro et al in U.S. Pat. No. 5,117,816 and Hays et al in U.S. Pat. No. 5,092,346. The use of struts of adjustable length to effect mandibular advance are taught by Lowe in U.S. Pat. No. 5,409,017 and Strong in U.S. Pat. Nos. 6,418,933 and 6,526,982. The use of hooks, posts or similar devices to connect a lower dentition engagement unit to an upper dentition engagement unit in a position of mandibular advance is taught by Gaskell in U.S. Pat. No. 6,845,774, Lampert in U.S. Pat. No. 5,823,194, Fenton in U.S. Pat. No. 5,499,633 and Haistrom in U.S. Pat. Nos. 5,365,945, 5,868, 138 6,041,784, 6,161,542 and 6,729,335. The use of elastic elements to apply a force to effect mandibular advancement is taught by Frantz et al in U.S. Pat. Nos. 5,947,724, 6,109,265, WO 2014/197430 and US 2011/0003262 and by Awde in US 2012/0251970.

To varying degrees, the devices referred to in the foregoing are expensive to purchase, are heavy, are bulky, are uncomfortable in use, are an impediment to speech and breathing, are an impediment to jaw movement, are difficult to clean and sanitise, are of limited effect, or are difficult to use, and require the services of specialized personnel for individual fitting and adjustment.

Specifically, in relation to applications employing forms of ramps or wedging elements fixed to an upper dentition engagement unit to effect mandibular advancement by exerting a force against the lower dentition or a lower dentition engagement unit, such applications may effect only a small degree of mandibular advancement. Where a larger degree of mandibular advancement is generated, the rate of displacement of the temporomandibular joint effected in a single jaw closure may cause discomfort in a subject. The grinding sensation as the ramps or wedging elements act upon the lower dentition or lower dentition engagement unit with jaw movement is regarded by many users as unpleasant.

In all of the cited examples in which they are employed to apply a force to effect mandibular advancement, elastic elements are connected at each side to the posterior parts of means to engage the mandibular dentition, and to the anterior parts of means to engage the maxillary dentition. The elastic elements are necessarily short and therefore suffer from a rapidly diminishing contractive force as mandibular displacement occurs.

The current invention was conceived with these shortcomings in mind.

SUMMARY OF THE INVENTION

The principal object of the present invention is to provide an oral device or splint to effect mandibular advancement for the purpose of alleviating snoring and sleep apnoea, the device applying a controlled and relatively unobtrusive force which is substantially sustained over the desired displacement distance, the force being easily tolerated by a subject during wakefulness, but sufficient to be effective when the subject has entered the sleep state.

Secondary objects of the present invention are to provide a device which is self-contained, light in weight and compact, which is easily cleaned and sanitised, which does not require special fitting and adjustment and which is easy to use.

According to an aspect of the invention, there is provided a mandibular advancement splint ('MAS') comprising: a pair of approximately arcuate dentition engagement units, each having a flat face for operatively abutting a complementary face of the other and an opposed dentition engagement face which is adapted to positively engage, as appropriate, all or part of the maxillary or mandibular dentition, the plane of abutment of said faces being arranged approximately normal to the sagittal plane, permitting sliding displacement of one said engagement unit relative to the other; and at least one elastic element configured to operatively exert a user-configurable urging force between said dentition engagement units so that said mandibular dentition engagement unit is urged anteriorly along said plane of abutment when said splint is in use.

Typically, said dentition engagement units are made from thermoplastic polyurethane (TPU), polyethylene terephthalate-glycol (PET-G), polymethyl-methacrylate (PMMA) or other suitable material in solid or laminated form.

Typically, each dentition engagement unit is configured to engage between 25 percent and 75 percent of the exposed depth of the maxillary and mandibular dentition.

Typically, one of said dentition engagement units incorporates at least two attachment pins or lugs configured to releasably receive the ends of at least one said elastic element.

Typically, one of said dentition engagement units incorporates at least two pins, lugs or rollers configured to releasably receive and provide a directional deflection of at least one said elastic element.

Typically, said pins, lugs or rollers are configured to minimise impedance of longitudinal displacement and/or extension or contraction through the minimisation of frictional effects.

Typically, said maxillary dentition engagement unit has formed in it a groove or channel passing completely around its anterior surface and adapted to freely accommodated and guide said at least one elastic element.

Typically, said attachment pins or lugs and said pins, lugs or rollers are located on said dentition engagement units as required to direct the urging forces of said at least one elastic element to urge said dentition engagement units into abutment and to urge said dentition engagement unit engaging said mandibular dentition anteriorly along said plane of abutment when said splint is in use.

Typically, said dentition engagement units are moulded from dental impressions made by a dental mechanic in the normal way or created directly by a user by several methods.

Typically, said at least one elastic element of extended length is employed to minimise to diminution of contractive force with mandibular advancement Typically, in embodiments in which a single elastic element is employed, it is directionally deflected by passing around pins, lugs or rollers located at the sides and towards the posterior extremity of the mandibular dentition engagement unit and thence passes in primary runs obliquely upwards to be accommodated as a loop within said groove or channel formed in and passing completely around the anterior surface of the maxillary dentition engagement unit.

Typically, shorter secondary runs of said elastic element pass from said pins, lugs or rollers to attachment pins or lugs located in first positions on the sides of the maxillary dentition engagement unit or in second positions located on the sides of the mandibular dentition engagement unit, the ends of the secondary runs of the elastic element being detachably fixed to attachment pins or lugs.

Typically, where the ends of said secondary runs of said elastic element are fixed to the maxillary dentition engagement unit, said attachment pins or lugs are located anteriorly of said pins, lugs or rollers by at least the maximum distance of mandibular displacement to be generated.

Typically, where the ends of said secondary runs of said elastic element are fixed to the mandibular dentition engagement unit, the attachment pins or lugs are located at or anteriorly of the mid length of said mandibular dentition engagement unit.

Typically, in embodiments in which two elastic elements are employed, they pass around said pins, lugs or rollers located at the sides and towards the posterior extremity of said mandibular dentition engagement unit and thence pass in primary runs obliquely upwards to attachment pins or lugs located on the side surfaces of the maxillary dentition engagement unit towards its anterior extremity and to which their first ends are detachably fixed.

Typically, shorter secondary runs of said two elastic elements pass from said pins, lugs or rollers to attachment pins or lugs located on the sides of the maxillary dentition engagement unit or located on the sides of the mandibular dentition engagement unit, the second ends of said elastic elements being detachably fixed to said attachment pins or lugs.

Typically, where the ends of the secondary runs of said two elastic elements are fixed to said maxillary dentition engagement unit, said attachment pins or lugs are located anteriorly of said pins, lugs or rollers by at least the maximum distance of mandibular displacement to be generated.

Typically, where the ends of the secondary runs of said two elastic elements are fixed to said mandibular dentition engagement unit, said attachment pins or lugs are located towards the anterior extremity of said mandibular dentition engagement unit.

Typically, said primary runs of said two elastic elements simultaneously act to urge the two said dentition engagement units into abutment while urging the mandibular dentition engagement unit towards anterior displacement.

Typically, shorter, obliquely upward secondary runs of said two elastic elements passing from said pins, lugs or rollers to attachment pins or lugs located on the sides of the maxillary dentition engagement unit simultaneously act to urge the two dentition engagement units into abutment while also urging said mandibular dentition engagement unit towards anterior displacement.

Typically, horizontal secondary runs of said two elastic elements provide additional length to ensure the maintenance of elastic tension during mandibular advancement.

Typically, suitable channels are preferably provided in the exterior surfaces of the maxillary and mandibular dentition engagement units to accommodate or substantially the several runs of said elastic elements and their elongational and lateral displacement.

Typically, said single elastic element or said two elastic elements are adapted to enable a user-configurable urging force.

Typically, said elastic element or elements are made from a plurality of elastic materials each having elastic moduli and/or elastic limits in order to provide variable levels of elastic force in accordance with said user-configurable urging force.

Typically, said elastic element or elements are made in varying widths and/or thicknesses in order to provide various levels of force and/or elasticity in accordance with said user-configurable urging force.

Typically, said elastic element or elements are made from a variety of materials varying along a length thereof, harder portions of said elastic elements being adapted to operatively engage and/or abut a pin, lug or roller of a said dentition engagement unit.

Typically, end zones of said elastic element or elements define a plurality of engagement apertures adapted to be engaged with said attachment pins or lugs to enable variation of said user-configurable urging force.

Typically, A said pin, lug or roller of a said dentition engagement unit incorporates a ratchet mechanism configured to facilitate said user-configurable urging force by enabling adjustment of travel of said elastic element or elements.

BRIEF DESCRIPTION OF THE DRAWINGS

The various aspects of the present invention will be more readily understood by reference to the following description of preferred embodiments given in relation to the accompanying drawings in which:

FIG. 1 is a side view of a cranium depicted with mandible in-situ and a schematically-depicted embodiment of the present invention in place;

FIG. 2 is a side view of the maxillary and mandibular dentition engagement units and elastic elements of an embodiment of the present invention, said elements shown in their positions prior to mandibular advancement;

FIG. 3 is a side view of the dentition engagement units of FIG. 2, said elements shown in their positions following mandibular advancement;

FIG. 4 is a side view of the embodiment of FIG. 2 with an alternative form of elastic elements, including an end zone incorporating a series of apertures engageable with attachment pins or lugs;

FIG. 5 is a side view of the embodiment of FIG. 2 incorporating a cover separating the buccal surfaces from said elastic elements and their attachments;

FIG. 5*a* is a fragmentary cross-sectional view of tabs and recesses employed to attach the cover of FIG. 5;

FIG. 6 is a fragmentary cross-sectional view of an attachment fitting employed to attach said elastic elements to said dentition engagement units;

FIG. 7 is a fragmentary cross-sectional view of said pins or lugs incorporating a roller for directional deflection of said elastic element or elements;

FIG. 8 is a fragmentary transverse cross-sectional view of the attachment fitting of FIG. 6 incorporated into a discrete band attachable to said maxillary and mandibular dentition engagement units;

DETAILED DESCRIPTION OF EMBODIMENTS

Figure 10:
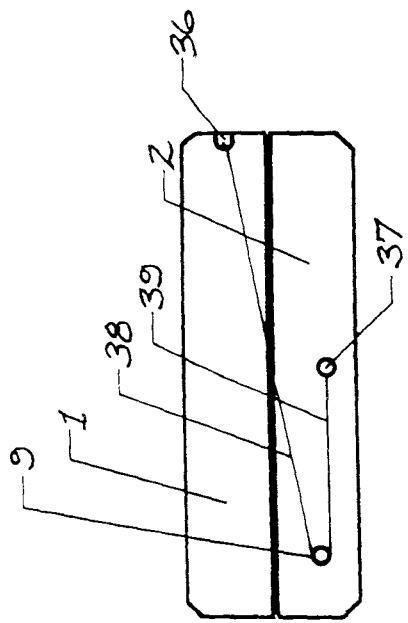
FIG. 10 is a schematic side view of another alternative embodiment of the elastic element of the present invention.

Further Features of the present invention are more fully described in the following description of several non-limiting embodiments thereof. This description is included solely for the purposes of exemplifying the present invention to the skilled addressee. It should not be understood as a restriction on the broad summary, disclosure or description of the invention as set out above. In the figures, incorporated to illustrate features of the example embodiment or embodiments, like reference numerals are used to identify like parts throughout.

With general reference to the accompanying figures, there is shown different embodiments of a mandibular advancement splint ('MAS') typically comprising a pair of dentition engagement units 1, 2, each having a face 3, 4 for operatively abutting a complementary face of the other, and an opposed dentition engagement face which is adapted to positively engage the maxillary and mandibular dentition. A plane of abutment of the faces 3, 4 is approximately normal to the sagittal plane to facilitate sliding displacement of one said dentition engagement unit relative to the other.

The exemplified MAS further includes at least one elastic element adapted to operatively exert a user-configurable urging force between dentition engagement units 1, 2 such that said mandibular dentition engagement unit is displaced anteriorly along said abutment plane relative to said maxillary dentition engagement unit when said splint is in use.

With reference now to FIG. 1, a side view of a cranium is depicted with mandible in-situ and an embodiment of the present invention in place engaged with the maxillary and mandibular dentition. The normal position 20 and dislocated position 21 of the temporomandibular joint are depicted, mandibular advancement in the range 5 to 10 millimetres normally being required to alleviate the symptoms of snoring and sleep apnoea.

With additional reference to FIGS. 2 and 3, maxillary dentition engagement unit 1 and mandibular dentition engagement unit 2 of the present invention are approximately arcuate in shape, each being provided with a flat face, respectively, 3, 4 which abuts a complementary flat face of the other and opposed dentition engagement surfaces (not shown) which are adapted to positively engage, as appropriate, all or part of the maxillary or mandibular dentition. The abutting plane of said flat faces is arranged more or less normal to the sagittal plane.

Said dentition engagement units are made from thermoplastic polyurethane (TPU), polyethylene terephthalate-glycol (PET-G), polymethyl-methacrylate (PMMA), or other suitable material in solid or laminated form as are well known in the field of dentistry and the like. The dentition engagement surfaces, commonly referred to as dental overlays, preferably engage between 25 percent and 75 percent of exposed tooth depth and are moulded by a dental mechanic from dental impressions in the manner well known in the art or created directly by a user employing several methods.

In a first such user-employed method (not shown), dentition engagement surfaces are created directly by a user by biting into a quantity of settable resin material provided in channels formed in said opposed faces of said dentition engagement units, the material then retaining an impression of the dentition during setting. Simple locating means are employed to maintain the two dentition engagement units in correct juxtaposition while the dental impressions are made by biting.

In a second such user-employed method (not shown), splint preforms of ethylene vinyl acetate or other thermoplastic material are heated to soften them, the heated splints are positioned over the user's dentition and pressure is applied to bring the softened material into conformity with the dentition. The re-shaped splints are removed when they have cooled, retaining the impression of the user's dentition. This is the so-called 'boil and bite' method of splint making.

In order to maintain elastic urging with mandibular advancement, a single-piece elastic element 12 is employed, said elastic element being removably fixed to attachment pins or lugs 7 at each side of the exterior surface of said maxillary dentition engagement unit, passing in secondary runs 8 obliquely downwards to pass over pins, lugs or rollers 9 located at each side of said mandibular dentition engagement unit and located posteriorly of said attachment pins or lugs, and thence passing in primary runs 10 obliquely upwards to pass in the form of a loop around a groove or channel 11 formed in and passing completely around the anterior surfaces of said maxillary dentition engagement unit.

In the preferred embodiment, said attachment pins or lugs are located adjacent the region of the second bicuspid/molar and the separation of said pairs of attachment pins of lugs and said pins, lugs or rollers in said dentition engagement units (measured parallel to the sagittal plane) is not less than the maximum distance of mandibular displacement desired, said secondary runs of said elastic element thus being more of less vertical (normal to the abutting surfaces of the dentition engagement units) at the point of maximum mandibular displacement.

Said obliquely downwards secondary runs of said elastic element simultaneously act to urge the two said dentition engagement units into abutment while urging said mandibular dentition engagement unit towards anterior displacement. Said obliquely upwards primary runs of said elastic element simultaneously act to urge the two said dentition engagement units into abutment while also urging said mandibular dentition engagement unit towards anterior displacement.

Obviously, increased posterior displacement of the location of said pins, lugs or rollers will ensure an increased or more sustained elastic urging of said mandibular dentition engagement unit towards the anteriorly advanced position. In the preferred embodiment, suitably-shaped channels 5, 6 are provided in the side, exterior surfaces of said maxillary and mandibular dentition engagement units to accommodate said primary and secondary runs of said elastic element and their elongational and lateral displacement.

In the preferred embodiment, suitable end fittings 22 are swaged at 14 to the ends of said elastic element, said end fittings being easily connected to said attachment pins or lugs. Said attachment pins and said pins for deflecting said elastic element, where employed, are made from a metal alloy material, have inner end parts embedded in said dentition engagement units and have rounded outer ends or head parts to minimise irritation of the buccal surfaces of a user. Said attachment lugs and said lugs for deflecting said elastic element, where employed, are formed from the parent material of said dentition engagement units and have similar rounded outer ends or head parts.

With additional reference to FIGS. 6, 7 and 8, in the preferred embodiment, said attachment pins or lugs and said pins, lugs or rollers are positioned within recesses 13 formed in the side surfaces of said dentition engagement units so as to minimise the possibility of irritation of the buccal surfaces of a user. It should be noted that said single-piece elastic element is easily removed from said dentition engagement units simply by dislodging it from groove 11 and disconnecting said end fittings from said attachment pins or lugs. In the preferred embodiment, the sides of groove 11 are provided with a small, local cut-away (not shown) at the anterior edge of said maxillary dentition engagement unit, said cut-away facilitating grasping of said elastic element with the fingers.

In alternative embodiments, said elastic element is made with a round, flat or other transverse cross-sectional shape, in single or multiple units and in a variety of elastomeric materials to provide greater or lesser elastically-contractive force. In other alternative embodiments, said elastic element is made with one part non-elastic or elastic to only a minor degree and one or more parts suitably elastic.

In another alternative embodiment, said elastic element is made in the form of a flat, narrow strap, part of which is provided with a series of apertures engageable with said attachment pins or lugs, said arrangement permitting said elastic element to be stretched to a greater or lesser extent to vary the elastic urging applied towards mandibular advancement. In all embodiments in which the use of single said elastic elements is described, two or more elastic elements may be employed.

Importantly, it is to be appreciated that elastic element/s 12 is typically configured to enable variation of said user-configurable urging force between dentition engagement units 1, 2. In one embodiment, said elastic element is made from a plurality of elastic materials, each having different elastic moduli and/or elastic limits in order to provide various levels of force and/or elasticity in accordance with said user-configurable urging force. In this embodiment, for example, said elastic element comprises two types of elastic material, one being more elastic up to a point to provide comfort to a user of the MAS, whilst the other is less elastic to provide the required urging force. In another embodiment, the shape of the elastic element 12 is used to provide such described functionality. For example, said elastic element is made with a narrower part to provide more elasticity and comfort to the user, and a wider part to provide the required urging force. Similarly, said pins, lugs or rollers of a dentition engagement unit 1, 2 are positioned and configured to facilitate variation of said user-configurable urging force (described below with reference to FIG. 12).

Similarly, as described in the foregoing paragraph, elastic element 12 defines varying widths and/or thicknesses along a zone or length thereof in order to provide various levels of force and/or elasticity in accordance with said user-configurable urging force. For example, elastic element 12 comprises a plurality of materials of varying hardness along a zone or length thereof, said harder parts of said elastic element being adapted to operatively engage and/or abut a pin, lug or roller of a dentition engagement unit. Elastic element 12 also defines a plurality of engagement apertures along end zones thereof to facilitate selective engagement with a said attachment pin or lug of a dentition engagement unit to enable variation of said user-configurable urging force.

With reference to FIG. 4, said single-piece elastic element is replaced by two elastic bands, the ends of each of which are engaged with attachment pins or lugs 7 located on the exterior surfaces of said maxillary dentition engagement unit adjacent the region of the second bicuspid/molar, are led obliquely downward in a secondary run 16 to pass over pins, lugs or rollers 9 located at each side of said mandibular dentition engagement unit and located posteriorly of said attachment pins or lugs, and thence in an obliquely upwards primary run 17 to allow the other ends of said elastic bands to be engaged with attachment pins or lugs 15 located on the exterior surfaces of said maxillary dentition engagement unit positioned approximately adjacent the canines or first bicuspids. Because said elastic bands are more highly stressed than said single elastic element, they are preferably replaced daily. In an exemplary embodiment, elastic elements 17 also define a plurality of engagement apertures 17b along end zones 17a of strap-like form thereof to facilitate selective engagement with attachment pin or lug 15 of a dentition engagement unit to enable variation of said user-configurable urging force.

To increase their effect, said elastic bands are optionally duplicated or triplicated or otherwise increased in number. Said elastic bands are similar in effect to said single elastic element, both said upward and downward runs simultaneously acting to urge the two said dentition engagement units into abutment while also urging said mandibular dentition engagement unit towards anterior displacement. Said elastic bands are made with different degrees of elastically contractive force and are often colour-coded to signify that difference.

In an alternative embodiment (not shown), said elastic element and said elastic bands are replaced with elastic ligatures of the type employed in orthodontic applications, said ligatures being made from an elastomer and comprising a sequence of small, annular elements joined directly together or joined by short straight elements, the degree of elasticity being determined by the length of said straight elements, said annular elements at each end being conveniently engaged with said attachment pins. Said elastic ligatures are normally colour-coded to indicate their elasticity.

With reference to FIG. 5 and FIG. 5a, a single-piece shield 18 made from a thin, stiffly-elastic polymer material encloses and is in close contact with said maxillary and mandibular dentition engagement units, covering said elastic element and said attachment pins or lugs and said pins, lugs or rollers and presenting a smooth, comfortable surface to the user's buccal surfaces. Band 19 passes completely around the anterior surface of said mandibular dentition engagement unit and flaps 20 on either side are elastically stressed so as to be continuously urged against the anterior surfaces of said maxillary dentition engagement unit.

In use, as mandibular advancement occurs, said shield slides forwardly on said maxillary dentition engagement unit and flaps 20 slide around the anterior surfaces of said maxillary dentition engagement unit. To secure said shield to said mandibular dentition engagement unit, small parts of its lower edges are extended and turned through 90 degrees to form tabs 18a that engage complementary recesses 23, 24, 44 formed in the lower exterior surfaces of said mandibular dentition engagement unit (as depicted in FIG. 3). In the preferred embodiment, said shield is made generally convex with only its upper and lower edges contacting the exterior surfaces of said dentition engagement units.

With reference again to FIG. 6, attachment pins 25 are securely fixed to maxillary dentition engagement unit 1 by the inner ends of their shanks 25 being upset (not shown) or turned through approximately 90 degrees (not shown) and embedded in said dentition engagement unit. Said attachment pins are each provided with a rounded outer end or head part 27 shaped to minimise irritation of the buccal surfaces of a user. Depending upon their thicknesses, said elastic element or said elastic bands may be accommodated substantially within recess 13 and said attachment pin shortened such that said head part protrudes only slightly above the exterior surface of said maxillary dentition engagement unit.

With reference to FIG. 7, pins 30 for directional deflection of said elastic element or elements are securely fixed to the side surfaces mandibular dentition engagement unit 2 by the inner end of their shanks 29 being upset (not shown) or turned through approximately 90 degrees (not shown) and embedded in said dentition engagement unit. Said pins are each provided with rounded outer end or head part 27 shaped to minimise irritation of the buccal surfaces of a user and, in the preferred embodiment, a roller 28 is rotationally supported on each said pin. Said roller is made in the form of a simple cylinder or in necked form, as illustrated and acts to provide free movement of said elastic element or elements or said elastic bands over said pins. Similarly, depending upon their thicknesses, said elastic element or elements or said elastic bands may be accommodated substantially within recess 13 and said attachment pin shortened such that said head part protrudes only slightly above the exterior surface of said maxillary dentition engagement unit.

With reference to FIG. 8, in an alternative embodiment, attachment pin or pin for directional deflection of said elastic element or elements 25 is securely fixed to mounting strip 31 by the inner end 32 of its shank being upset (not shown) or turned through 90 degrees (as depicted) and embedded in said mounting strip. Said mounting strip is made from a suitable polymer material and is bonded to either said maxillary or mandibular dentition engagement unit in the desired position. In the preferred embodiment, a shallow channel 33 is provided in the exterior surface of said maxillary or mandibular dentition engagement unit to assist in locating said mounting strip. Also in the preferred embodiment, the exterior surfaces of said mounting strip are made smooth and rounded to minimise irritation of the buccal surfaces of a user.

In an alternative embodiment (not shown), said attachment pins or lugs are provided in multiple units positioned anteriorly or posteriorly of the typical position depicted in FIG. 2. Similarly, said pins, lugs or rollers are provided in multiple units positioned anteriorly or posteriorly of the typical position depicted in FIG. 2. Said multiple attachment pins or lugs and said multiple pins, lugs or rollers allow said elastic element or elements or said elastic bands to be installed in a variety of positions for best effect.

In the preferred embodiment (not shown), said attachment lugs and said lugs for directional deflection of said elastic element or elements or elastic bands are mushroom-shaped with the shank thickened to increase its strength. In an alternative embodiment (not shown), said attachment pins are replaced by hooks, said hooks having a point turned inwardly to a small degree and an elongated and flattened external surface, both features being designed to minimise irritation of the buccal surfaces of a user.

Figure 9:
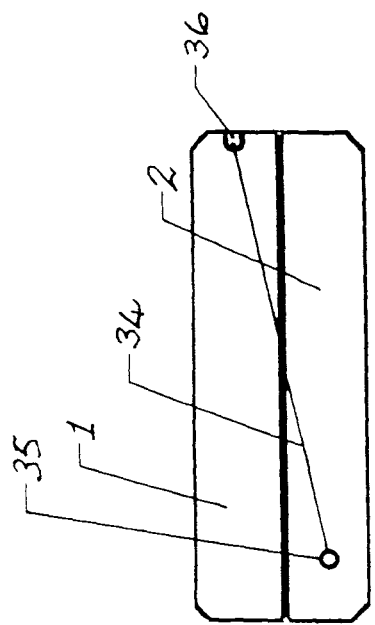
FIG. 9 is a schematic side view of an alternative embodiment of the elastic element of the present invention.

With reference to FIG. 9, the ends of single-piece elastic element 34 are fixed to attachment pins or lugs 35 located on each side of mandibular dentition engagement unit 2 towards the posterior end, said elastic element passing anteriorly in upwardly angled primary runs 34 to pass in a loop around the anterior end of maxillary dentition engagement unit 1 through groove 11. In the preferred embodiment, suitably-shaped channels (not shown) of the type numbered 5, 6 in FIG. 3 are provided in the side, exterior surfaces of said maxillary and mandibular dentition engagement units to accommodate or substantially accommodate said runs of said elastic element, said channels being of sufficient width to accommodate other than elongational displacement of said elastic element.

With reference to FIG. 10, the ends of single-piece elastic element 38, 39 are fixed to attachment pins or lugs 37 located on each side of mandibular dentition engagement unit 2 in or anteriorly of a medial position, said elastic element passing posteriorly in horizontal secondary runs 39 more or less parallel to the abutting faces of said dentition engagement units and thence around pins, lugs or rollers 9 to pass anteriorly in upwardly angled primary runs 38 to pass in a loop around the anterior end of maxillary dentition engagement unit 1 through groove 11. Also in the preferred embodiment, suitably-shaped channels (not shown) of the type numbered 5, 6 in FIG. 3 are provided in the side, exterior surfaces of said maxillary and mandibular dentition engagement units to accommodate elongational and lateral displacement of said runs of said elastic element.

Figure 11:
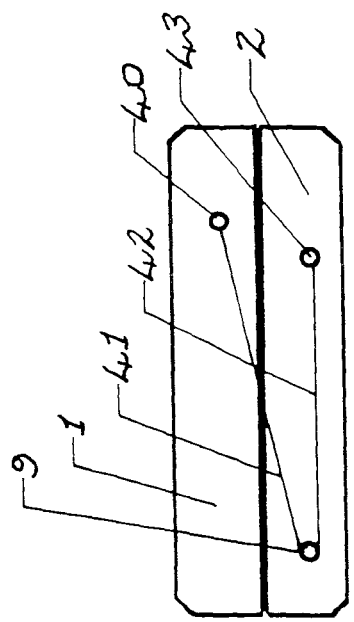
FIG. 11 is a schematic side view of an alternative embodiment of the present invention incorporating two discrete elastic elements.

With reference to FIG. 11, the lower ends of discrete elastic elements 41, 42 are fixed to attachment pins or lugs 43 located on each side of mandibular dentition engagement unit 2 and positioned towards the anterior end, said elastic elements passing posteriorly in horizontal secondary runs 42 more or less parallel to the abutting faces of said dentition engagement units and thence around pins, lugs or rollers 9 to pass anteriorly in upwardly angled primary runs 41, the ends of which are fixed to attachment pins or lugs 40 located towards the anterior extremity of maxillary dentition engagement unit 1. Also in the preferred embodiment, suitably-shaped channels (not shown) of the type numbered 5, 6 in FIG. 3 are provided in the side, exterior surfaces of said maxillary and mandibular dentition engagement units to accommodate elongational and lateral displacement of said runs of said elastic element.

In the embodiment depicted in FIG. 9, angled runs 34 of said single-piece elastic element urge mandibular dentition engagement unit 2 anteriorly while urging together the abutting faces of said dentition engagement units, the extended length of said elastic element acting to minimise diminution of elastic urging as mandibular displacement occurs. Similarly, in the embodiment depicted in FIG. 10, angled primary runs 38 of said single-piece elastic element urge mandibular dentition engagement unit 2 anteriorly while urging together the abutting faces of said dentition engagement units, the extra lengths of horizontal secondary runs 39 of said elastic element acting to minimise diminution of elastic urging as mandibular displacement occurs. Also similarly, in the embodiment depicted in FIG. 11, angled primary runs 41 of said discrete elastic elements urge mandibular dentition engagement unit 2 anteriorly while urging together the abutting faces of said mandibular advancement units, the extra lengths of horizontal secondary runs 42 of said elastic elements acting to minimise diminution of elastic urging as mandibular displacement occurs.

In alternative embodiments, said attachment pins or lugs moulded into or formed on said dentition engagement units are replaced by headed pins the threaded shanks of which are screwably engaged with threaded bores in said dentition engagement units, or which have tapered shanks which are frictionally engaged with complementary tapered recesses in said dentition engagement units, or which have shanks with locally thickened parts which are pushed through sprung elements within bores in said dentition engagement units, or which have shanks with sprung elements which are pushed through constricted parts of bores in said dentition engagement units, or which have shanks provided with transverse projections which engage complementary shaped recesses in bores in said dentition engagement units in a bayonet-and-socket arrangement, said pins being installed in said dentition engagement unit either manually or by use of a suitable tool.

In the embodiment depicted in FIG. 2, in use, maxillary dentition engagement unit 1 and mandibular dentition engagement unit 2 and elastic element 12 are taken from sterile storage and said dentition engagement units are brought together with their said flat faces in registration and abutment. End fittings 22 of said elastic element are connected to attachment pins or lugs 7, said elastic element then being stretched to pass over pins, lugs or rollers 9 and to pass upwardly and anteriorly to be engaged as a loop in groove 11.

When the subject is prepared for sleep, said maxillary and mandibular dentition engagement units are held by the subject in registration and placed in the oral cavity to engage the maxillary and mandibular dentition. The forces applied by said elastic element are quite tolerable and are able to be consciously opposed by the subject. When the subject has entered the sleep state, the mandibular musculature relaxes and mandibular advancement commences. Where said elastic bands are employed, they are installed separately in the same manner as said elastic element, but with their anterior ends engaged with attachment pins or lugs 15 located at the anterior ends of said maxillary dentition engagement unit. The procedures for installation of one or more said elastic elements or elastic bands in the embodiments depicted in FIGS. 9, 10 and 11 are obvious in light of the immediately preceding explanation.

Figure 12:
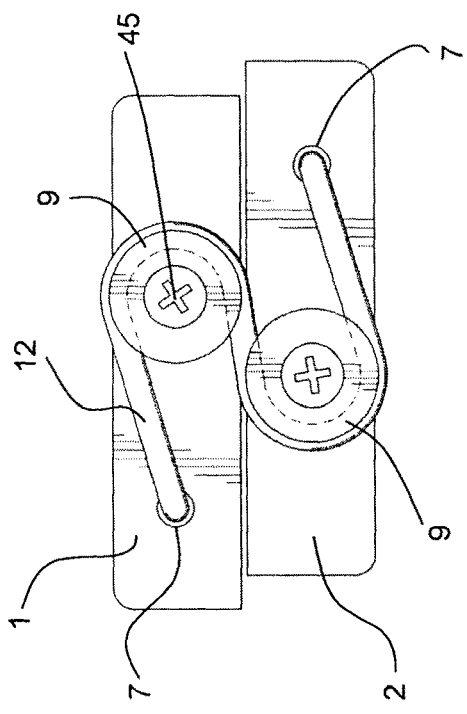
FIG. 12 is a diagrammatic side view representation, shown in exaggerated fashion, of a pin, lug or roller of the MAS which is configured to minimise impedance of longitudinal displacement and/or extension or contraction of an elastic element.

As briefly described in the foregoing and with reference to FIG. 12, in embodiments of the invention, a pin, lug or roller 9 is configured to minimise impedance of longitudinal displacement and/or extension or contraction of elastic element 12, that is, to minimise friction of displacement of the elastic element thereon. For example, as shown in exaggeration in FIG. 12 for ease of description, pin, lug or roller 9 optionally includes a bearing to reduce friction, coating with a friction-reducing material, or journaling for rotation, etc. In addition, a pin, lug or roller 9 is generally located or positioned on a dentition engagement unit 1, 2 according to urging force requirements between said dentition engagement units and the production of mandibular advancement anteriorly along said abutment plane. Accordingly, depending on requirements, each dentition engagement unit includes a plurality of pins, lugs or rollers 9 located at various positions thereon, the positions depending upon urging force requirements and the value and/or direction of such force.

Figure 13:
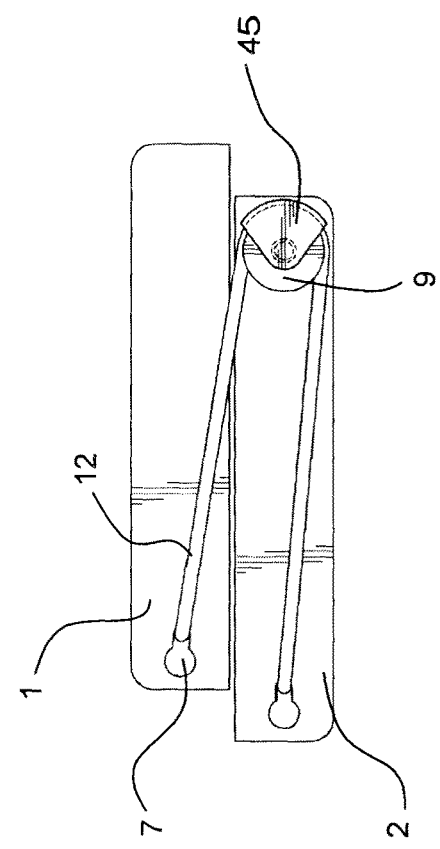
FIG. 13 is a diagrammatic side view representation of one possible embodiment of the MAS, having a pin, lug or roller of a dentition engagement unit which is configured to detachably secure or retain the elastic element thereto.
Figure 14:
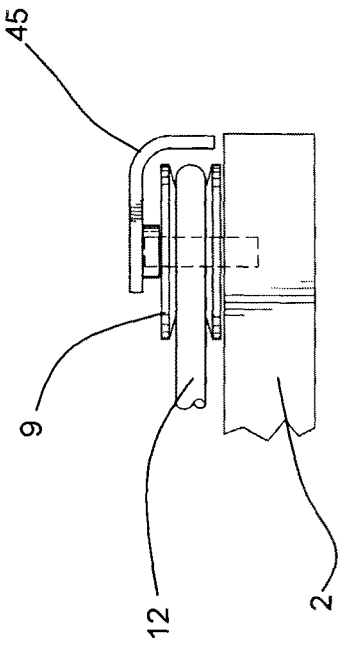
FIG. 14 is a diagrammatic top view representation of a pin, lug or roller of a dentition engagement unit which is configured to detachably secure or retain the elastic element.

With reference to FIGS. 13 and 14, a pin, lug or roller 9 of dentition engagement units 1, 2 is also configured to releasably secure or retain elastic element 12 thereto whilst minimising impedance of longitudinal displacement and/or extension or contraction of said elastic element. In the exemplified embodiment, dentition engagement unit 2 incorporates a locating element 45 to secure or retain elastic element 12 to pin, lug or roller 9, whilst also forming a smooth surface to minimise irritation or injury of the user's buccal surfaces. Locating element 45 is optionally resiliently flexible to permit elastic element 12 to be urged past it onto pin, lug or roller 9.

Figure 15:
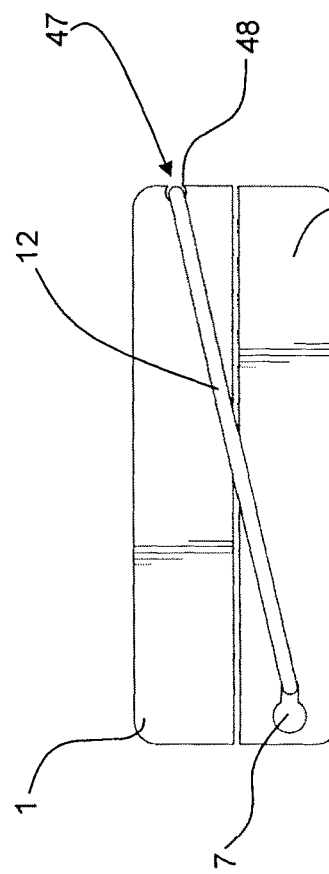
FIG. 15 is a diagrammatic side view representation of one possible embodiment of the MAS, wherein a dentition engagement unit is configured to detachably secure or retain the elastic element thereto.

Similarly, with reference to FIG. 15 (and as briefly described in the foregoing), groove or channel 47 passes fully around the anterior surface of maxillary dentition engagement unit 1 to accommodate elastic element 12, said groove having a central zone 48 of slightly narrower width than the width or cross-sectional diameter of said elastic element in its relaxed state, said narrower central zone acting to retain said elastic element within said groove or channel after being urged through said narrower zone.

Applicant regards it as particularly advantageous that the MAS in accordance with aspects of the present invention provides for arrangements and configurations whereby elastic element 12 provides the necessary urging force to facilitate mandibular advancement, whilst also facilitating comfort to a user of the MAS and allowing user-configuration of the urging force to regulate the effects of using said MAS.

Optional embodiments of the present invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth. In the example embodiments, well-known processes, well-known device structures, and well-known technologies are not described in detail, as such will be readily understood by the skilled addressee.

The use of the terms "a", "an", "said", "the", and/or similar referents in the context of describing various embodiments (especially in the context of the claimed subject matter) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. As used herein, the term "and/or" includes any and all combinations of one or more of the associated listed items. No language in the specification should be construed as indicating any non-claimed subject matter as essential to the practice of the claimed subject matter.

Spatially relative terms, such as "inner," "outer," "beneath," "below," "lower," "above," "upper," and the like, may be used herein for ease of description to describe the relationship of one element or feature to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

It is to be appreciated that reference to "one example" or "an example" of the invention, or similar exemplary language (e.g., "such as") herein, is not made in an exclusive sense. Various substantially and specifically practical and useful exemplary embodiments of the claimed subject matter are described herein, textually and/or graphically, for carrying out the claimed subject matter.

Accordingly, one example may exemplify certain aspects of the invention, whilst other aspects are exemplified in a different example. These examples are intended to assist the skilled person in performing the invention and are not intended to limit the overall scope of the invention in any way unless the context clearly indicates otherwise. Variations (e.g. modifications and/or enhancements) of one or more embodiments described herein might become apparent to those of ordinary skill in the art upon reading this application. The inventor expects skilled artisans to employ such variations as appropriate, and the inventor(s) intends for the claimed subject matter to be practised other than as specifically described herein.

Any method steps, processes, and operations described herein are not to be construed as necessarily requiring their performance in the particular order discussed or illustrated, unless specifically identified as an order of performance. It is also to be understood that additional or alternative steps may be employed.

What is claimed is:

1. A device forming a mandibular advancement splint 'MAS' for alleviation of snoring and sleep apnoea, the device comprising:
   a pair of discrete, approximately arcuate maxillary and mandibular dentition engagement units, each having a flat face in sliding abutment with a complementary flat face of the other and an opposed dentition engagement face adapted to positively engage all or part of a maxillary or mandibular dentition, a plane of abutment of said flat faces being arranged more or less normal to a sagittal plane;

rollers located at sides and towards a posterior extremity of said mandibular dentition engagement unit;

attachment pins or lugs located at sides and towards a posterior extremity of said maxillary dentition engagement unit or the posterior extremity of said maxillary dentition engagement unit, anteriorly of said rollers by at least a maximum distance of mandibular displacement to be generated; and a single elastic element passing around the rollers and then obliquely upwards in primary runs accommodated as a loop within a groove or channel for longitudinal movement or other than elongational displacement and the groove or channel formed in and passing completely around an anterior surface of said maxillary dentition engagement unit, shorter lengths of said elastic element passing in secondary runs from said rollers to be detachably fixed to the attachment pins or lugs of said maxillary dentition engagement unit, said device configured to cause anterior displacement of a mandible from a normal position of a temporomandibular joint in a range 5 to 10 millimetres.

2. The device of claim 1 further comprising a single-piece shield made from a thin, stiffly-elastic polymer material, which encloses and is in close contact with said maxillary and mandibular dentition engagement units, covering said elastic element and said attachment pins or lugs and said rollers and presenting a smooth, comfortable surface to buccal surfaces of a user.

3. The device of claim 2 wherein a band of said shield passes completely around an anterior surface of said mandibular dentition engagement unit, flaps passing to either side of said maxillary dentition engagement unit, said flaps being elastically stressed so as to be continuously urged against the anterior surfaces of said unit; during mandibular advancement, said shield sliding forwardly on said maxillary dentition unit with said flaps remaining in contact with the anterior surfaces of said maxillary dentition engagement unit.

4. The device of claim 2 wherein said shield is secured to said mandibular dentition engagement unit by small parts of its lower edges being extended and turned inwardly through 90 degrees to form tabs that engage complementary recesses formed in lower exterior surfaces of said mandibular dentition engagement unit.

5. The device of claim 2 wherein said shield is convex such that only its upper and lower edges contact said dentition engagement units.

6. The device of claim 1 wherein suitable channels are provided in exterior surfaces of said maxillary and mandibular dentition engagement units to accommodate or substantially accommodate said runs of said elastic element, said channels being widened to accommodate other than elongational displacement of said elastic element or elements during said mandibular advancement.

7. The device of claim 6 in which the exterior surfaces of said dentition engagement units are locally cut away to facilitate grasping of said elastic element with fingers.

8. The device of claim 1 wherein said groove or channel formed in and passing completely around the anterior surface of the maxillary dentition engagement unit has a central zone of slightly narrower width than a width or cross-sectional diameter of said elastic element in its relaxed state, such that said elastic element is retained within said groove or channel after being urged through said narrower zone.

9. The device of claim 1 wherein pairs of said attachment pins or lugs are located on the sides of said maxillary dentition engagement unit adjacent the region of a second bicuspid to first molar, a separation between said pairs of attachment pins of lugs and said rollers, measured parallel to the sagittal plane, being not less than the maximum distance of mandibular displacement desired, such that said secondary runs of said elastic element are more or less normal to said plane of abutment at a point of maximum mandibular displacement.

10. The device of claim 1 wherein said rollers are configured to minimise impedance of longitudinal displacement and/or extension or contraction of said elastic element by minimising sliding or rolling friction of said elastic element thereon, said rollers being configured to releasably secure or retain said elastic element thereto.

11. The device of claim 1 wherein the single said elastic element has an installed length selected to minimise diminution of contractive force with mandibular advancement.

12. The device of claim 1 wherein said primary runs of said elastic element simultaneously act to urge said dentition engagement units into abutment while urging said mandibular dentition engagement unit towards anterior displacement; said shorter, secondary runs passing between said mandibular and maxillary dentition engagement units, being more steeply angled, simultaneously act to urge said dentition engagement units more firmly into abutment while also urging said mandibular dentition engagement unit towards anterior displacement.

13. The device of claim 1 further comprising additional elastic elements made from a plurality of elastic materials, each having different elastic moduli and/or elastic limits in order to provide various levels of force and/or elasticity in accordance with said user-configurable urging force; and wherein said additional elastic elements are made with varying widths and/or thicknesses along lengths thereof in order to provide variable levels of elastic force in accordance with said user-configurable urging force; and wherein said additional elastic elements are made with a plurality of materials of varying hardness along lengths thereof, harder parts of said elastic elements being adapted to operatively engage and/or abut roller; and wherein said additional elastic elements are made with a plurality of engagement apertures along end zones thereof to facilitate their selective engagement with said attachment pins or lugs to enable variation of said user-configurable urging force.

14. The device of claim 1 wherein suitable fittings are swaged to ends of said elastic element, said end fittings being easily connectable to said attachment pins or lugs.

15. The device of claim 1 wherein said attachment pins or lugs to which ends of said elastic element are fixed and said rollers over which said elastic element pass are substantially accommodated within recesses formed in the side surfaces of said dentition engagement units, said attachment pins or lugs and said rollers being shortened such that their head parts protrude above the exterior surface of said maxillary dentition engagement units so as to minimise irritation of the buccal surfaces of a user.

16. The device of claim 1 wherein said elastic element is replaceable with elastic ligatures of the type employed in orthodontic applications, said ligatures being made from an elastomer and comprising a sequence of small, annular elements joined directly together or joined by short straight elements, a degree of elasticity being determined by a length of said straight elements, said annular elements at each end being conveniently engaged with said attachment pins or lugs.

17. The device of claim 1 wherein said attachment pins are securely fixed to said dentition engagement units by embedding of inner ends of their shanks, said inner ends having been upset or turned through approximately 90 degrees; said attachment pins or lugs being made from a suitable metal alloy material, having inner, end parts embedded in said dentition engagement units and rounded outer ends or head parts to minimise irritation of buccal surfaces of a user.

18. The device of claim 1 wherein said rollers for directionally deflecting said elastic element is rotationally supported on shanks of pins having inner ends of their shanks embedded in said mandibular engagement unit, said rollers being made in the form of simple cylinders or in concave (necked) form, said rollers acting to provide free movement of said elastic element over said pins.

19. The device of claim 1 wherein said attachment pins or lugs and said rollers are securely fixed to a separate mounting strip made from a suitable polymer material, said mounting strip being bonded to said maxillary and/or mandibular dentition engagement units in appropriate positions; a shallow channel being provided in exterior surfaces of said maxillary or mandibular dentition engagement units to locate and partially accommodate said mounting strip, exterior surfaces of said mounting strip being made smooth and rounded to minimise irritation of buccal surfaces of a user.

20. The device of claim 1 wherein said attachment pins or lugs are replaceable by hooks, said hooks having a point turned inwardly to a degree and an elongated and flattened external surface, both features being designed to minimise irritation of buccal surfaces of a user.

21. The device of claim 1 wherein said attachment pins take the form of headed pins which have threaded shanks screwably engaged with threaded bores in said dentition engagement units; or which have tapered shanks which are frictionally engaged with complementary tapered recesses in said dentition engagement units; or which have shanks with locally thickened parts which are pushed through sprung elements within bores in said dentition engagement units; or which have shanks with sprung elements which are pushed through constricted parts of bores in said dentition engagement units; or which have shanks provided with transverse projections which engage complementary shaped recesses in bores in said dentition engagement units in a bayonet-and-socket arrangement; said pins being installed in said dentition engagement unit either manually or by use of a suitable tool.

* * * * *